(12) United States Patent
Larson et al.

(10) Patent No.: US 6,893,421 B1
(45) Date of Patent: May 17, 2005

(54) CATHETER SHAFT ASSEMBLY

(75) Inventors: Scott Larson, St. Louis Park, MN (US); Justin Crank, Minneapolis, MN (US); Matthew Hawk, Otsego, MN (US); Bradley Slaker, Greenfield, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/635,083

(22) Filed: Aug. 8, 2000

(51) Int. Cl.[7] ............................................. A61M 5/178
(52) U.S. Cl. ................................................. 604/164.01
(58) Field of Search ............................. 604/19–21, 27, 604/93.01, 115, 116, 117, 158–159, 161–162, 164.01, 164.06–164.09, 164.11, 164.12, 165.01–165.02, 166.01, 173, 2 A, 272, 523, 528, 533; 606/1, 167, 172, 185; 607/1–3; 600/433–435, 564, 585

(56) References Cited

U.S. PATENT DOCUMENTS

| | | | |
|---|---|---|---|
| 4,578,061 A | 3/1986 | Lemelson | 604/164 |
| 4,658,817 A | 4/1987 | Hardy | 128/303.1 |
| 4,760,131 A | 7/1988 | Sundsmo et al. | 530/356 |
| 4,790,311 A | 12/1988 | Ruiz | 128/303.1 |

(Continued)

FOREIGN PATENT DOCUMENTS

| | | |
|---|---|---|
| DE | 296 09 350 U 1 | 10/1996 |
| DE | 195 37 084 A 1 | 4/1997 |
| EP | 0 689 467 B1 | 10/1993 |
| EP | 0 692 276 A2 | 1/1996 |

(Continued)

OTHER PUBLICATIONS

Mirhoseini et al., Abstract entitled "Transventricular Revascularization by Laser", *Lasers in Surgery and Medicine*, 2(2), 1982, 1 page.
Gal et al., Abstract entitled "Analysis of Photoproducts Free Radicals and Particulate Debris Generated . . . ", *Lasers in Surgery and Medicine*, 11(2) 1991, 1 page.
Isner, J., Abstract entitled "Right Ventricular Myocardial Infarction", *JAMA*, v259, n5, Feb. 5, 1988, 12 pages.
Pickering et al., Abstract entitled "Proliferative Activity in Peripheral and Coronary Atherosclerotic Plaque . . . ", *J. Clin. Invest.*, ISSN 0021–9738, Apr. 1993, 1 page.
Vineberg et al., "Creation of Intramyocardial Pathways to Channel Oxygenated Blood Between Ventricular Arteriolar Zones", *Canad. Med. Ass. J.*, vol. 96, Feb. 4, 1967, 3 pages.
Vineberg, A., "Results of 14 Years' Experience in the Surgical Treatment of Human Coronary Artery Insufficiency", *Canad. Med. Ass. J.*, vol. 92, Feb. 13, 1965, 8 pages.

(Continued)

*Primary Examiner*—LoAn H. Thanh
(74) *Attorney, Agent, or Firm*—Kenyon & Kenyon

(57) ABSTRACT

A catheter shaft assembly is disclosed. A catheter shaft in accordance with the present invention comprises a first elongate shaft having an inner surface defining a lumen, a second elongate shaft slidingly disposed within the lumen of the first elongate shaft, at least one interstitial member disposed between the inner surface of the first elongate shaft and the outer surface of the second elongate shaft.

6 Claims, 12 Drawing Sheets

U.S. PATENT DOCUMENTS

| | | | |
|---|---|---|---|
| 4,857,057 A | * 8/1989 | Sanagi | 604/170.01 |
| 4,896,671 A | 1/1990 | Cunningham et al. | 128/642 |
| 4,973,321 A | 11/1990 | Michelson | |
| 5,047,026 A | 9/1991 | Rydell | 606/48 |
| 5,093,877 A | 3/1992 | Aita et al. | 385/34 |
| 5,261,889 A | * 11/1993 | Laine et al. | 600/104 |
| 5,287,861 A | 2/1994 | Wilk | 128/898 |
| 5,353,800 A | 10/1994 | Pohndorf et al. | 128/673 |
| 5,354,279 A | 10/1994 | Hofling | 604/164 |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,405,376 A | 4/1995 | Mulier et al. | 607/127 |
| 5,431,649 A | 7/1995 | Mulier et al. | 606/41 |
| 5,464,395 A | 11/1995 | Faxon et al. | 604/96 |
| 5,486,161 A | * 1/1996 | Lax et al. | 604/22 |
| 5,522,815 A | 6/1996 | Durgin, Jr. et al. | 606/50 |
| 5,551,427 A | 9/1996 | Altman | 128/642 |
| 5,569,462 A | 10/1996 | Martinson et al. | 424/424 |
| 5,591,159 A | 1/1997 | Taheri | 606/15 |
| 5,593,394 A | 1/1997 | Kanesaka et al. | |
| 5,593,405 A | 1/1997 | Osypka | 606/15 |
| 5,601,586 A | 2/1997 | Fucci et al. | 606/180 |
| 5,601,588 A | 2/1997 | Tonomura et al. | 606/185 |
| 5,607,405 A | 3/1997 | Decker et al. | 604/264 |
| 5,620,414 A | 4/1997 | Campbell, Jr. | 604/22 |
| 5,672,174 A | 9/1997 | Gough et al. | 606/41 |
| 5,681,308 A | 10/1997 | Edwards et al. | 606/41 |
| 5,683,366 A | 11/1997 | Eggers et al. | 604/114 |
| 5,697,882 A | 12/1997 | Eggers et al. | 604/114 |
| 5,700,259 A | 12/1997 | Negus et al. | 606/14 |
| 5,713,894 A | 2/1998 | Murphy-Chutorian et al. | 606/15 |
| 5,725,521 A | 3/1998 | Mueller | 606/7 |
| 5,725,523 A | 3/1998 | Mueller | 606/15 |
| 5,762,631 A | 6/1998 | Klein | |
| 5,766,164 A | 6/1998 | Mueller et al. | 606/15 |
| 5,769,843 A | 6/1998 | Abela et al. | 606/10 |
| 5,797,870 A | 8/1998 | March et al. | 604/49 |
| 5,807,388 A | 9/1998 | Jeevanandam et al. | 606/15 |
| 5,810,836 A | 9/1998 | Hussein et al. | 606/108 |
| 5,827,203 A | 10/1998 | Nita | 601/2 |
| 5,840,059 A | 11/1998 | March et al. | 604/53 |
| 5,845,646 A | 12/1998 | Lemelson | |
| 5,871,495 A | 2/1999 | Mueller | 606/185 |
| 5,873,366 A | 2/1999 | Chim et al. | 128/898 |
| 5,873,855 A | 2/1999 | Eggers et al. | 604/114 |
| 5,911,729 A | 6/1999 | Shikhman et al. | 606/181 |
| 5,913,853 A | 6/1999 | Loeb et al. | 606/15 |
| 5,921,982 A | 7/1999 | Lesh et al. | 606/41 |
| 5,925,033 A | 7/1999 | Aita et al. | 606/7 |
| 5,931,848 A | 8/1999 | Saadat | 606/167 |
| 5,944,716 A | 8/1999 | Hektner | 606/45 |
| 5,947,989 A | 9/1999 | Shikhman et al. | 606/180 |
| 5,964,754 A | 10/1999 | Osypka | 606/37 |
| 6,042,581 A | 3/2000 | Ryan et al. | 606/45 |
| 6,045,565 A | 4/2000 | Ellis et al. | 606/167 |
| 6,053,911 A | 4/2000 | Ryan et al. | 606/33 |
| 6,053,924 A | 4/2000 | Hussein | 606/108 |
| 6,056,742 A | 5/2000 | Murphy-Chutorian et al. | 606/11 |
| 6,056,743 A | 5/2000 | Ellis et al. | 606/15 |
| 6,086,582 A | 7/2000 | Altman et al. | |
| 6,217,554 B1 | 4/2001 | Green | |

FOREIGN PATENT DOCUMENTS

| | | |
|---|---|---|
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | * 4/1998 |
| WO | WO 98/17186 | 4/1998 |
| WO | WO 98/18391 | 5/1998 |
| WO | WO 98/27877 | 7/1998 |
| WO | WO 98/39038 | 9/1998 |
| WO | WO 99/04850 | 2/1999 |
| WO | WO 99/04851 | 2/1999 |
| WO | WO 99/29251 | 6/1999 |
| WO | WO 99/39624 | 8/1999 |
| WO | WO/99/44656 | * 9/1999 |
| WO | WO 99/44656 | 9/1999 |
| WO | WO 00/15146 | 3/2000 |
| WO | WO 00/16704 | 3/2000 |

OTHER PUBLICATIONS

Vineberg et al., "The Ivalon Sponge Procedure for Myocardial Revascularization", Surgery, vol. 47, No. 2, Feb. 1960, pp. 268–289.

Vineberg et al., "Treatment of Acute Myocardial Infarction by Endocardial Resection", Surgery, vol. 57, No. 6, Jun. 1965, pp. 832–835.

Walter et al., "Treatment of Acute Myocardial Infarction by Transmural Blood Suply from the Ventricular Cavity", European Surgical Research, 3:130–138 (1971).

Khazei et al., "Myocardial Canalization", The Annals of Thoracic Surgery, vol. 6, No. 2, Aug. 1968, pp. 163–171.

Hershey et al., "Transmyocardial Puncture Revascularization", Geriatrics, Mar. 1969, pp. 101–108.

Press Release dated Oct. 21, 1996, "Doctor's Demonstrate Proof of Blood Flow Through Open TMR Channels Created with PLC Systems . . . ", 1 page.

Press/News Release dated Oct. 10, 1996, "Texas Fieart Institute Presents Study Comparing the Use of CO2 . . . ", 1 page.

Goldman et al., "Nonoperative Portacaval Shunt in Swine", Investigative Radiology, vol. 25, No. 5, May 1990, 5 pages.

Schumacher et al., "Induction of Neoangiogenesis is Ischemic Myocardium by Human Growth Factors", Clinical Investigation and Reports, Dec. 1, 1997, 6 pages.

Article entitled "Gene therapy improves leg circulation—next step heart?", $70^{th}$ Scientific Sessions, published on or before Nov. 2, 1998, 2 pages.

Winslow, R., "Genetic Techniques Succeed in Treating Patients with Obstructed Blood Vessels", The Wall Street Journal, published on or before Nov. 2, 1998, 2 pages.

Kolata, G., "Gene Therapy Gives Blood a Path Around Leg Blockages, Researchers Say", The New York Times, Nov. 10, 1997, 2 pages.

Mack et al., "Cardiopulmonary Support and Physiology", The Journal of Thoracic and Cardiovascular Surgery, vol. 115, No. 1, Jan., 1998, 10 pages.

* cited by examiner

CATHETER SHAFT ASSEMBLY

FIELD OF THE INVENTION

The present invention relates generally to intravascular catheters for performing medical procedures. More particularly, the present invention relates to shaft assemblies for use in intravascular catheters. Still, more particularly, the present invention relates to catheter shaft assemblies for use in injection catheters.

BACKGROUND OF THE INVENTION

Intravascular catheters are currently utilized in a wide variety of minimally-invasive or percutaneous medical procedures. Generally, an intravascular catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed.

Typically, a percutaneous procedure begins with the step of inserting a distal portion of the catheter into the patient's vasculature at a convenient location. Once the distal portion of the catheter has entered the patient's vascular system the physician may urge the distal tip forward by applying longitudinal forces to the proximal portion of the catheter. Frequently the path taken by a catheter through the vascular system is tortuous, requiring the catheter to change direction frequently. While advancing the catheter through the tortuous path of the patient's vasculature, the physician must steer the distal end of the catheter. During a percutaneous procedure, the physician typically is not able to manipulate the distal portion of the catheter directly. For this reason, physicians typically must steer the distal end of the catheter by applying torsional forces to the proximal portion of the catheter.

Injection catheters are a type of catheter which may be used to inject therapeutic or diagnostic agents into various target tissues within the human body. An advantage of injection catheters is that the target tissue may be accessed utilizing minimally invasive surgical techniques. As with other types of catheters, the physician typically is not able to manipulate the distal portion of an injection catheter directly.

In many applications the target tissue is within a wall of an organ such as the stomach or the heart. When the target tissue is within the wall of an organ it is often desirable to inject the therapeutic or diagnostic agent into the tissue proximate the center of the organ wall. If the needle of the injection catheter inadvertently passes through the wall, the therapeutic or diagnostic agents dispensed from the distal end of the needle will not be effectively delivered to the target tissue.

One example of a medical procedure involving the delivery of a therapeutic and/or diagnostic agent to a targeted portion of a patient's body is the treatment of esophageal varices. This is a condition in which blood vessels of the esophagus are enlarged and may potentially burst. For such a procedure, a therapeutic agent is injected into the varix. When treating an esophageal varix, the agent may be a coagulant such as sodium morrhuate. When a coagulant is injected into a varix, it causes it to occlude. An injection catheter may be used to deliver the therapeutic agent in order to minimize the invasive nature of the procedure.

In a similar procedure, an injection catheter may be utilized in the treatment of ulcers in the stomach lining. With such treatment, an injection catheter may be used to deliver drugs such as sclerosing or vasoconstrictive agents. These drugs typically clot or occlude the bleeding tissue to stop bleeding or to reduce the possibility of a blood vessel bursting.

Injection catheters may also be used to inject therapeutic or diagnostic agents into the heart. Examples of agents delivered to the heart include genes, proteins, or drugs. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma, which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The tortuous path and small diameter of these blood vessels limit access to the stenotic lesions. The sheer number and small size of these stenotic lesions make techniques such as cardiovascular by-pass surgery, angioplasty, and atherectomy impractical When techniques which treat individual lesions are not practical, percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency energy delivered by a catheter having one or more electrodes near its distal end. After the wound has been created, therapeutic agents are sometimes ejected into the heart chamber from the distal end of a catheter.

Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenesis. After the wound has been created, therapeutic agents which are intended to promote angiogenesis are sometimes ejected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

SUMMARY OF THE INVENTION

The present invention relates generally to intravascular catheters for performing medical procedures. More particularly, the present invention relates to shaft assemblies for use in intravascular catheters. Still, more particularly, the present invention relates to catheter shaft assemblies for use in injection catheters.

A shaft assembly in accordance with an exemplary embodiment of the present invention comprises a first elongate shaft having an inner surface defining a lumen, a second elongate shaft slidingly disposed within the lumen of the first elongate shaft, and an interstitial member disposed between the inner surface of the first elongate shaft and the outer surface of the second elongate shaft.

In one embodiment of a shaft assembly in accordance with the present invention a plurality of longitudinal ribs extend beyond an inner surface of the first elongate shaft. These longitudinal ribs preferably contact the outer surface of the second elongate shaft.

In an additional embodiment of a shaft assembly in accordance with the present invention a radial rib extends beyond the inner surface of the first elongate shaft. The radial rib preferably contacts the outer surface of the second elongate shaft. When the radial rib is in contact with outer surface of second elongate shaft there is preferably no substantial gap between the radial rib and the outer surface of the second elongate shaft.

An additional embodiment of a shaft assembly in accordance with the present invention includes a coil comprising a wire forming a plurality of turns. Each turn of the coil is disposed between the inner surface of the first elongate shaft and the outer surface of the second elongate shaft.

In an additional embodiment of a shaft assembly in accordance with the present invention the second elongate shaft has a plurality of projections extending beyond the outer surface of the second elongate shaft. When the second elongate shaft is disposed within the lumen defined by the first elongate shaft, these projections preferably contact the inner surface of the first elongate shaft.

An injection catheter in accordance with an exemplary embodiment of the present invention includes a first elongate shaft having an inner surface defining a lumen. A second elongate shaft having an outer surface is slidingly disposed within the lumen of the first elongate shaft. In this exemplary embodiment, the second elongate shaft includes a point and an injection orifice proximate its distal end. Also in this exemplary embodiment, an interstitial member is disposed between the inner surface of the first elongate shaft and the outer surface of the second elongate.

In many applications it is desirable to advance the distal end of the second elongate shaft by a known distance relative to the distal end of the first elongate shaft. For example, when a physician wishes to inject a fluid into the wall of an organ. In one embodiment of a catheter in accordance with the present invention, a slider is fixed to the second elongate shaft proximate the proximal end thereof. Also in this embodiment, a portion of the slider is disposed within a cavity defined by a housing which is preferably fixed to the first elongate shaft proximate the proximal end thereof. Also in a preferred embodiment, a plurality of indicia are disposed on a face of the housing proximate the slider.

A physician utilizing the catheter in a surgical procedure may move the distal end of the second elongate shaft a known distance relative to the distal end of the first elongate shaft. For example, a physician may urge the slider distally while visually observing the travel of the slider relative to the indicia of the housing. The movement of the slider is translated via the second elongate shaft to the distal end thereof.

In a preferred embodiment there is substantially a one-to-one relationship between the movement of the slider relative to the indicia of the housing and the movement of the distal end of the second elongate shaft relative to the distal end of the first elongate shaft. In a particularly preferred embodiment, the presence of an interstitial member between the outer surface of the second elongate shaft and the inner surface of the first elongate shaft directs the motion of the second elongate shaft in a substantially longitudinal direction. Also in a particularly preferred embodiment, the presence of the interstitial member between the outer surface of the second elongate shaft and the inner surface of the first elongate shaft substantially precludes lateral movement of the second elongate shaft relative to the first elongate shaft. Thus, it is assured that there will be substantially a one-to-one relationship between the movement of the slider relative to the indicia of the housing and the movement of the distal end of the second elongate shaft relative to the distal end of the first elongate shaft.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
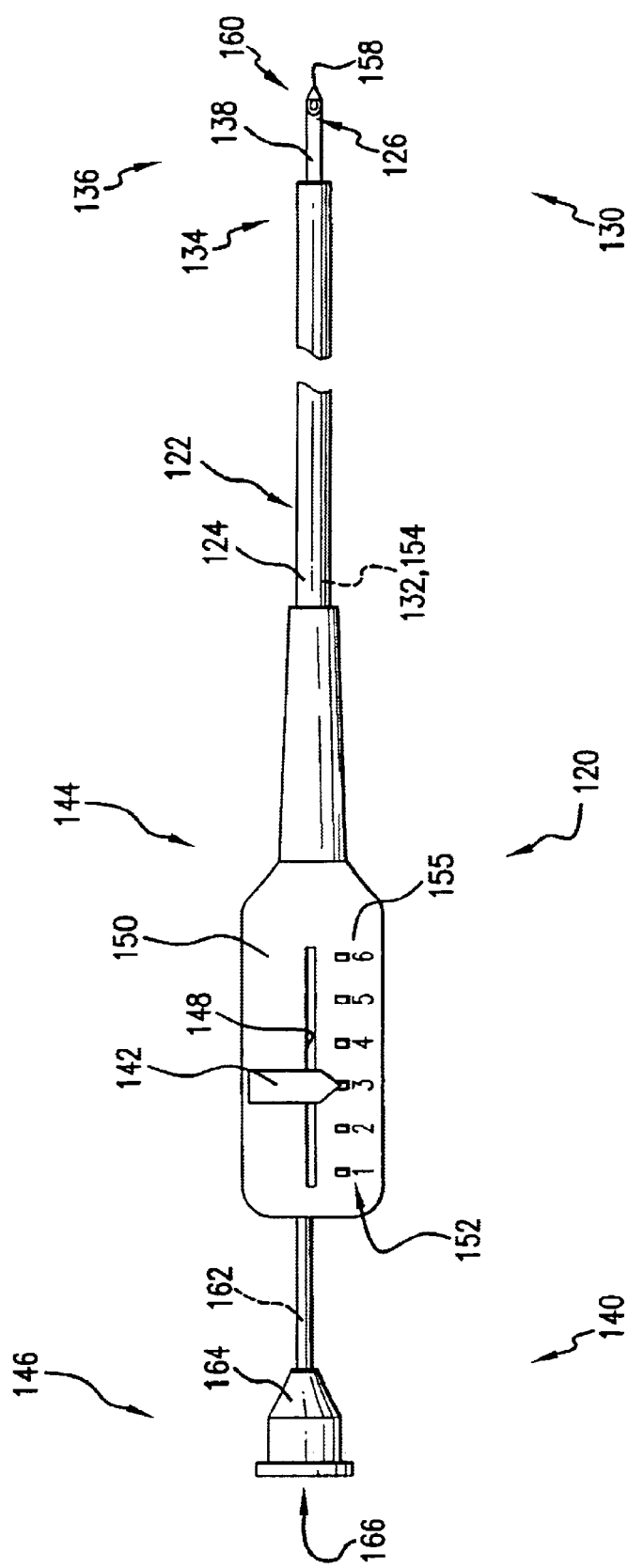
FIG. 1 is a plan view of a catheter including a shaft assembly in accordance with the present invention.

FIG. 1 is a plan view of a catheter 120 including a shaft assembly 122 in accordance with the present invention. Shaft assembly 122 comprises a first elongate shaft 124 having a distal end 134, a proximal end 144, and an inner surface 154 defining a lumen 132. Shaft assembly 122 also includes a second elongate shaft 126 slidingly disposed within lumen 132 of first elongate shaft 124. Catheter 120 also includes a distal end 130, and a proximal end 140.

Second elongate shaft 126 has an outer surface 138, distal end 136, and a proximal end 146. In many applications it is desirable to advance distal end 136 of second elongate shaft 126 by a known distance relative to distal end 134 of first elongate shaft 124. In the embodiment of FIG. 1, a slider 142 is fixed to second elongate shaft 126 proximate proximal end 146 thereof. In the embodiment of FIG. 1, a portion of slider 142 is disposed within a cavity 148 defined by a housing 150. In a presently preferred embodiment, housing 150 is fixed to first elongate shaft 124 proximate proximal end 144 thereof. Also in a preferred embodiment, a plurality of indicia 152 are disposed on a face 154 of housing 150 proximate slider 142.

A physician utilizing catheter 120 in a surgical procedure may move distal end 136 of second elongate shaft 126 a known distance relative to distal end 134 of first elongate shaft 124. For example, a physician may urge slider 142 distally while visually observing the travel of slider 142 relative to indicia 152 of housing 150. The movement of slider 142 is translated via second elongate shaft 126 to distal end 136 thereof.

In a preferred embodiment there is substantially a one-to-one relationship between the movement of slider 142 relative to indicia 152 of housing 150 and the movement of distal end 136 of second elongate shaft 126 relative to distal end 134 of first elongate shaft 124. In a particularly preferred embodiment, the presence of an interstitial member 156 between outer surface 138 of second elongate shaft 126 and inner surface 154 of first elongate shaft 124 directs the motion of second elongate shaft 126 in a substantially longitudinal direction. Also in a particularly preferred embodiment, the presence of interstitial member 156 between outer surface 138 of second elongate shaft 126 and inner surface 154 of first elongate shaft 124 substantially precludes lateral movement of second elongate shaft 126 relative to first elongate shaft 124. Thus, it is assured that there will be substantially a one-to-one relationship between the movement of slider 142 relative to indicia 152 of housing 150 and the movement of distal end 136 of second elongate shaft 126 relative to distal end 134 of first elongate shaft 124.

In the embodiment of FIG. 1, second elongate shaft 126 forms a point 158 proximate distal end 136 thereof. Second elongate shaft also defines an injection port 160 proximate point 158. A hub 164 is disposed about second elongate shaft 126 proximate proximal end 146 thereof. Hub 164 defines a proximal port 166. In a preferred embodiment, proximal port 166 is in fluid communication with injection port 160 via an injection lumen 162 defined by second elongate shaft 126.

Catheter 120 of FIG. 1 may be generally referred to as an injection catheter. It is to be appreciated that a catheter in accordance with the present invention may comprise various types of catheters without deviating from the spirit and scope of the present invention.

In a preferred embodiment, second elongate shaft 126 of catheter 120 comprises hypodermic tubing. Second elongate shaft 126 may comprise various metallic and non-metallic materials without deviating from the spirit and scope of the present invention. Examples of metallic materials which may be suitable in some applications include stainless steel, and nickel-titanium alloy. Examples of non-metallic materials which may be suitable in some applications are included in the list below which is not exhaustive:

polycarbonate, poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly (phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

In a preferred embodiment, first elongate shaft 124 of catheter 120 comprises an elongate tubular member including a reinforcement member (e.g., braided or coiled wire). Second elongate shaft 126 may comprise various metallic and non-metallic materials without deviating from the spirit and scope of the present invention. Examples of metallic materials which may be suitable in some applications include stainless steel, and nickel-titanium alloy. Examples of non-metallic materials which may be suitable in some applications include: polyethylene (PE), polypropylene (PP), polyvinylchloride (PVC), polyurethane, polytetrafluoroethylene (PTFE), polyether block amide (PEBA), polyamide, and polyimide.

Figure 2:
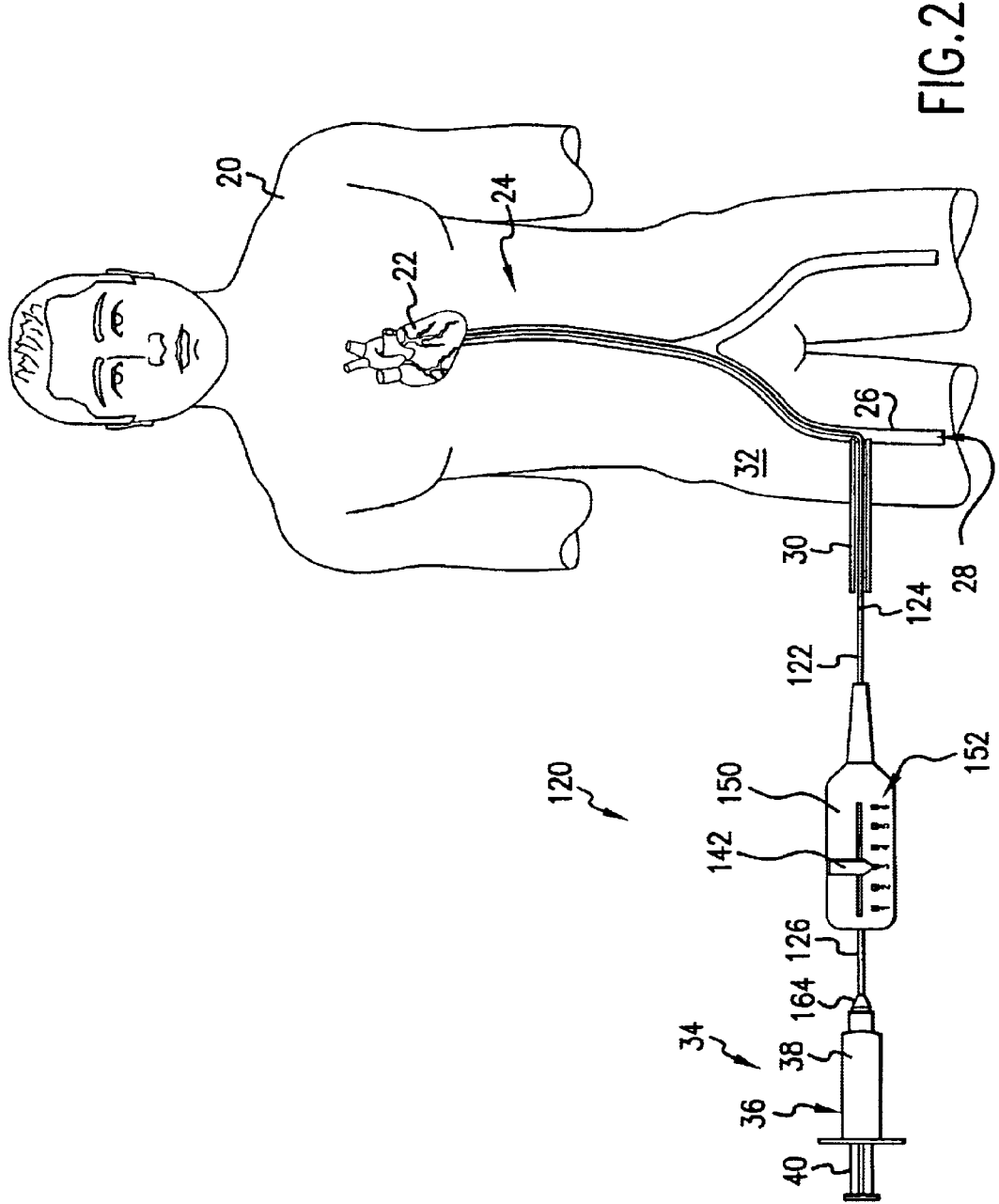
FIG. 2 is a diagrammatic view including the catheter of FIG. 1 and a patient.

FIG. 2 is a diagrammatic view including catheter 120 of FIG. 1 and a patient 20. Patient 20 has a heart 22 and a vascular system 24 including a blood vessel 26 defining a blood vessel lumen 28. An access sheath 30 is partially disposed within a leg 32 of patient 20. A distal end of access sheath 30 is disposed within blood vessel lumen 28 of blood vessel 26. Access sheath 30 may aid in the introduction of catheter 120 into blood vessel lumen 28.

As shown in FIG. 2, a portion of catheter 120 is disposed within blood vessel lumen 28 of blood vessel 26. Distal end 130 (not visible in FIG. 2) of catheter 120 is disposed within heart 22 of patient 20. In a preferred embodiment, distal end 130 of catheter 120 is disposed proximate a wall of heart 22.

In the embodiment of FIG. 2, a fluid source 34 is coupled to hub 164 disposed about second elongate shaft 126 of catheter 120. In the embodiment of FIG. 2, fluid source 34 includes a variable volume chamber 36 defined by a body 38. In a preferred embodiment, variable volume chamber 36 is in fluid communication with injection lumen 162 of second elongate shaft 126. A plunger 40 is slidingly disposed within variable volume chamber 36. Urging the plunger distally has the effect of urging fluid into injection lumen 162 of second elongate shaft 126. A number of energy sources may be utilized to urge plunger 40 distally. Energy sources which may be suitable in some applications include springs, compressed gas, a human being, and electricity. Various additional embodiments of fluid source 34 are possible without deviating from the spirit and scope of the present invention. Examples of fluid sources which may be suitable in some applications include syringes, peristaltic pumps, and an I.V. bag with pressure applied to an outer surface thereof.

A method of injecting a fluid into heart 22 of patient 20 may be described with reference to FIG. 2. The distal end of access sheath 30 may be inserted into blood vessel lumen 28 of blood vessel 26. Distal end 130 of catheter 120 may be inserted into the lumen of access sheath 30. Distal end 130 of catheter 120 may be advanced through access sheath 30 and into blood vessel lumen 28 of blood vessel 26. Catheter 120 may be urged forward through vascular system 24 of patient 20 until distal end 130 is proximate the target tissue (e.g., a wall of heart 22). In FIG. 2 it may be appreciated that shaft assembly 122 of catheter 120 is bent in a plurality of locations to conform with a tortuous path defined by vascular system 24.

In a preferred method, distal end 136 of second elongate shaft 126 is disposed within lumen 132 of first elongate shaft 124 during the above steps. Once distal end 130 of catheter 120 is positioned proximate the target tissue, second elongate shaft 126 may be advanced so that point 158 penetrates the bodily tissue at the target site. With injection port 160 of second elongate shaft 126 disposed within the target tissue, fluid may be urged into the target tissue. For example, force may be applied to plunger 40 urging fluid out of fluid source 34 and into injection lumen 162 of second elongate shaft 126. The addition of fluid from fluid source 34 results in the injection of fluid into the target tissue.

In many applications it is desirable to advance point 158 and injection port 160 into the target tissue by a known distance. A physician may advance point 158 and injection port 160 into the target tissue by urging slider 142 distally. A physician may determine the depth of penetration by visually observing the travel of slider 142 relative to indicia 152 of housing 150.

The movement of slider 142 is translated via second elongate shaft 126 to point 158 formed by second elongate shaft 126 proximate the distal end 136 thereof. In a preferred embodiment there is substantially a one-to-one relationship between the movement of slider 142 relative to indicia 152 of housing 150 and the movement of distal end 136 of second elongate shaft 126 relative to distal end 134 of first elongate shaft 124. In a particularly preferred embodiment, the presence of interstitial member 156 between outer surface 138 of second elongate shaft 126 and inner surface 154 of first elongate shaft 124 directs the motion of second elongate shaft 126 in a substantially longitudinal direction.

The fluid injected into the target area may include various therapeutic or diagnostic agents adapted to treat the medical condition which the physician is treating. It is to be appreciated that methods in accordance with the present invention may be used in the treatment of a number of medical conditions. For example, methods and devices of performing percutaneous myocardial revascularization (PMR) in accordance with the present invention have been envisioned. For example, a plurality of wounds may be created in hibernating tissue of the heart. These wounds may be created by injecting a fluid into the tissue of the heart. As a result of these wounds, there will be increased blood flow to the myocardium caused in part by the body's healing response to the wound. One healing response of the body is sometimes referred to as angiogenesis. In addition to promoting increased blood flow, it is also believed that PMR improves a patient's condition through denervation. Denervation is the elimination of nerves. The creation of wounds during this procedure results in the elimination of nerve endings which were previously sending pain signals to the brain as a result of hibernating tissue.

Suitable wounds may be created by injecting a fluid such as water, saline, or ringers solution into the heart tissue. Wound formation and revascularization of myocardial tissue may be enhanced by injecting a fluid including a therapeutic agent into the tissue of the heart. Examples of therapeutic agents which may be suitable include growth factors, drugs and caustic agents. The fluid injected into the heart tissue may also include a radiopaque material. Injecting a radiopaque material into the wound effectively marks the locations which have been treated. This will aid the physician in procedures which are performed percutaneously using fluoroscopic equipment.

In the exemplary embodiment of FIG. 2, catheter 120 may be utilized to inject fluid into heart 22 of patient 20. It is to be appreciated that catheter 120 may be utilized in the treatment of various medical conditions occurring in various locations in the body. For example, catheter 120 may be used in the treatment of esophageal varices, a condition in which blood vessels of the esophagus are enlarged and may potentially burst. For such a procedure, injection port 160 would be disposed proximate the enlarged varix and an appropriate agent would be injected into the varix. When treating an esophageal varice, the agent may be a coagulant such as sodium morrhuate. When a coagulant is injected into a varix, it causes the occlusion thereof.

Figure 3:
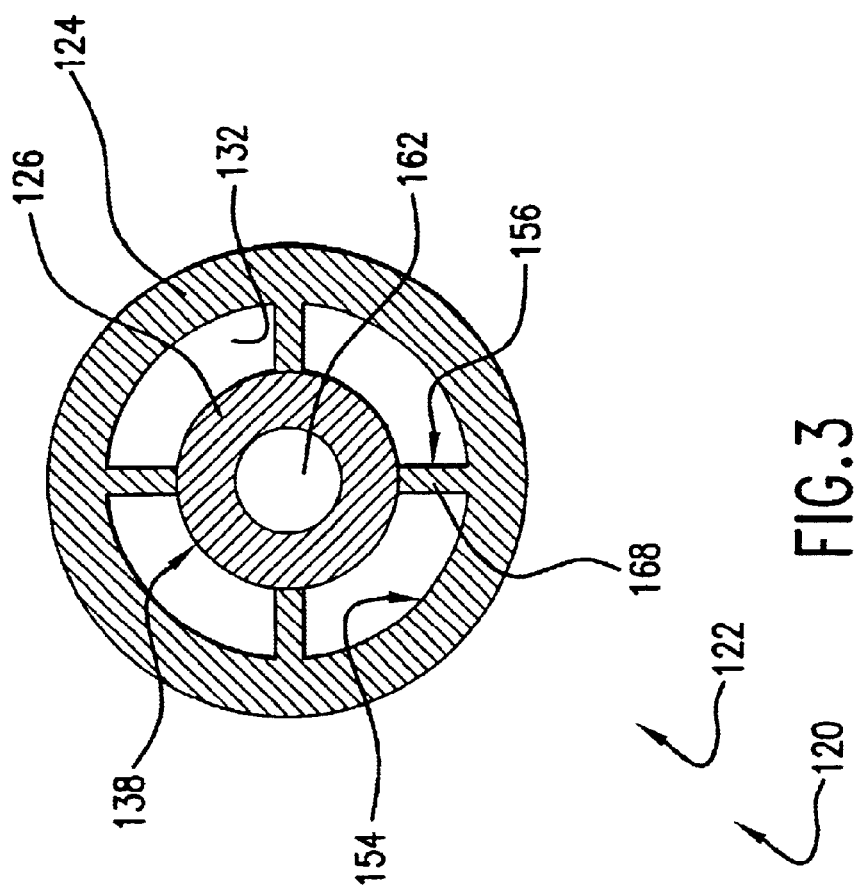
FIG. 3 is a lateral cross section view of the shaft assembly of the catheter of FIG. 1 and FIG. 2.

FIG. 3 is a lateral cross section view of shaft assembly 122 of catheter 120 of FIG. 1 and FIG. 2. As described above, shaft assembly 122 includes second elongate shaft 126 which is disposed within lumen 132 defined by first elongate shaft 124. In FIG. 3 it may be appreciated that a plurality of interstitial members 156 extend between first elongate shaft 124 and second elongate shaft 126. In the embodiment of FIG. 3, each interstitial member comprises a longitudinal rib 168. Each longitudinal rib 168 extends beyond an inner surface 154 of first elongate shaft 124 and contacts an outer surface 138 of second elongate shaft 126. Since longitudinal ribs 168 are in contact with outer surface 138 of second elongate shaft 126 it may be appreciated that there is substantially no gap between longitudinal ribs 168 and second elongate shaft 126. In a presently preferred embodiment, the gap between second elongate shaft 126 and each longitudinal rib 168 is, for example, between zero and 0.05 mm. Embodiments of the present invention are possible in which there is an interference fit between longitudinal ribs 168 and second elongate shaft 126. In FIG. 3, it may also be appreciated that second elongate shaft 126 defines an injection lumen 162.

Figure 4:
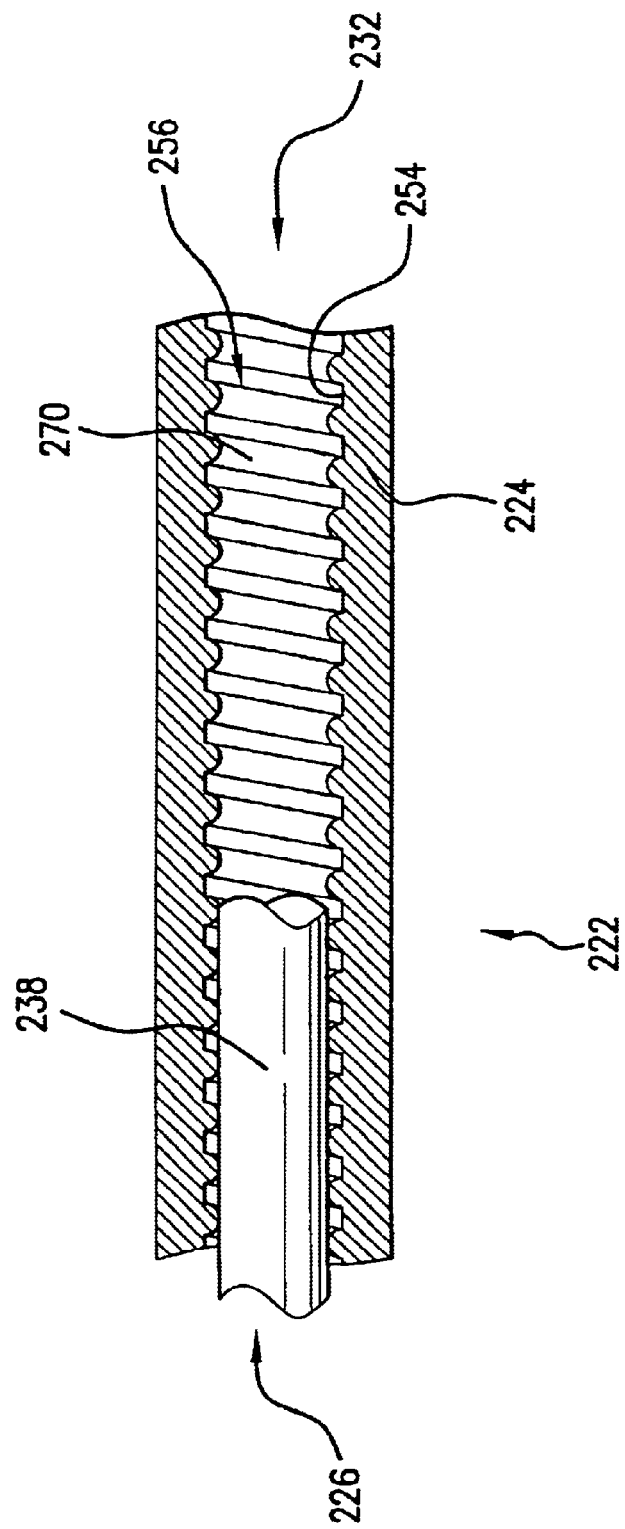
FIG. 4 is a partial cross section view of an additional embodiment of a shaft assembly in accordance with the present invention.

FIG. 4 is a partial cross section view of an additional embodiment of a shaft assembly 222 in accordance with the present invention. Shaft assembly 222 includes a second elongate shaft 226 disposed within a lumen 232 defined by an inner surface 254 of a first elongate shaft 224. First elongate shaft 224 also includes a plurality of interstitial members 256 extending beyond inner surface 254 of first elongate shaft 224. In the embodiment of FIG. 4, each interstitial member comprises a radial rib 270. As shown in FIG. 4, each radial rib 270 contacts an outer surface 238 of second elongate shaft 226. Since radial ribs 270 are in contact with outer surface 238 of second elongate shaft 226 it may be appreciated that there is substantially no gap between radial ribs 270 and second elongate shaft 226. In a presently preferred embodiment, the gap between second elongate shaft 226 and each radial rib 270 is, for example, between zero and 0.05 mm. Embodiments of the present invention are possible in which there is an interference fit between radial ribs 270 and second elongate shaft 226.

Figure 5:
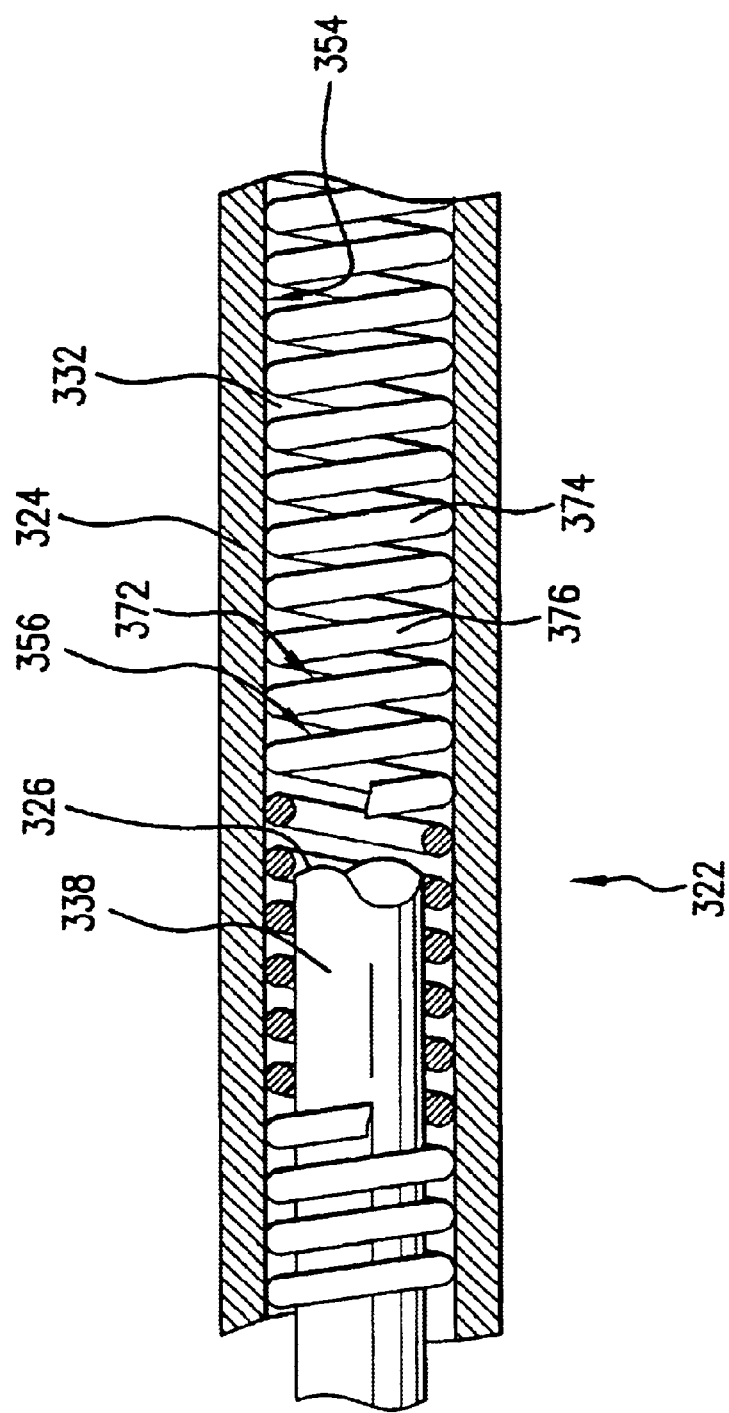
FIG. 5 is a partial cross section view of an additional embodiment of a shaft assembly in accordance with the present invention.

FIG. 5 is a partial cross section view of an additional embodiment of a shaft assembly 322 in accordance with the present invention. Shaft assembly 322 includes a first elongate shaft 324 having a lumen 332 defined by an inner surface 354 thereof. A second elongate shaft 326 and an interstitial member 356 are disposed within lumen 332 of first elongate shaft 324. In the embodiment of FIG. 5, interstitial member comprises a coil 372 comprising a wire 376 forming a plurality of turns 374. As shown in FIG. 5, each turn 374 of coil 372 is disposed between inner surface 354 of first elongate shaft 324 and outer surface 338 of second elongate shaft 326. In the embodiment of FIG. 5, each turn 374 is in contact with inner surface 354 of first elongate shaft 324 and outer surface 338 of second elongate shaft 326.

Figure 6:
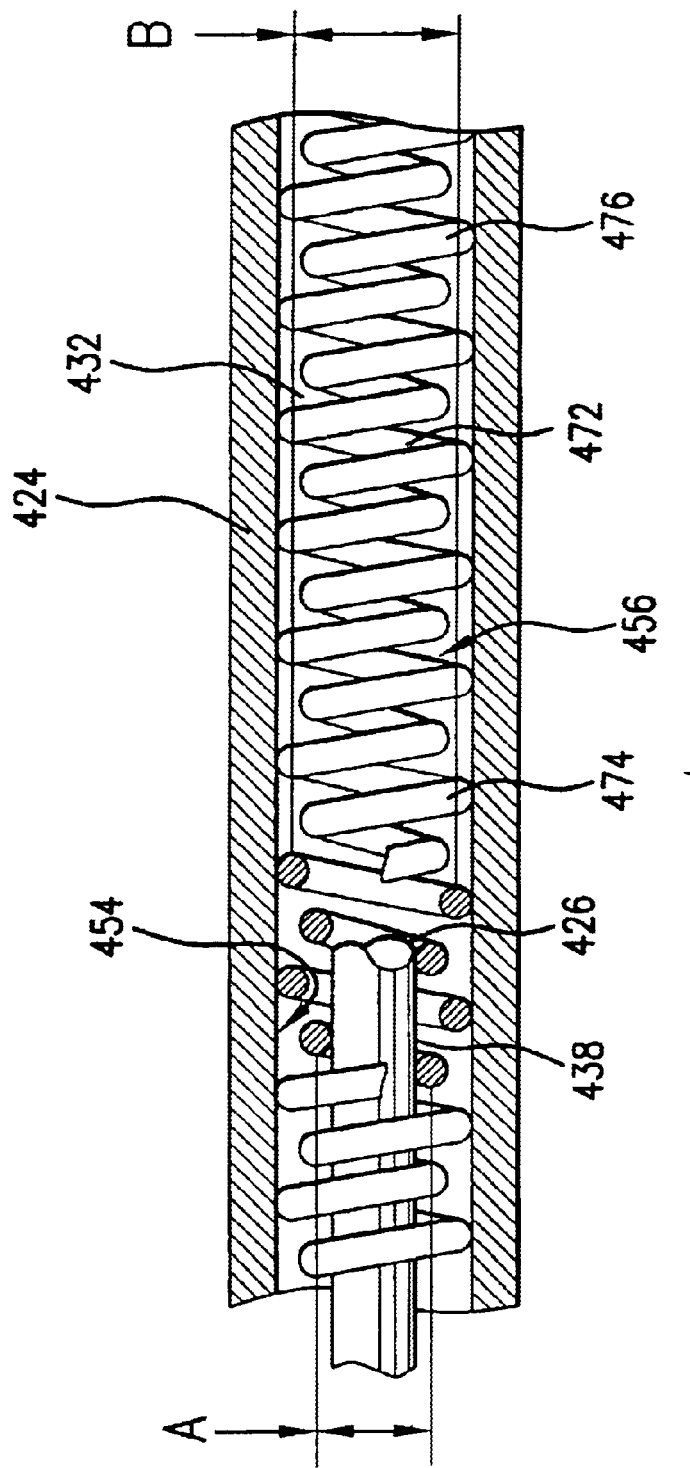
FIG. 6 is a partial cross section view of an additional embodiment of a shaft assembly in accordance with the present invention.

FIG. 6 is a partial cross section view of an additional embodiment of a shaft assembly 422 in accordance with the present invention. Shaft assembly 422 includes a first elongate shaft 424 having a lumen 432 defined by an inner surface 454 thereof. A second elongate shaft 426 and an interstitial member 456 are disposed within lumen 432 of first elongate shaft 424. In the embodiment of FIG. 6, interstitial member comprises a coil 472 comprising a wire 476 forming a plurality of turns 474.

In the embodiment of FIG. 6, coil 472 has a first pitch diameter A and a second pitch diameter B. In the embodiment of FIG. 6, coil 472 is preferrably adapted to contact outer surface 438 of second elongate shaft 426 with a plurality of turns 474. Also in the embodiment of FIG. 6, coil 472 is preferably adapted to contact inner surface 454 of first elongate shaft 424 with a plurality of turns. For example, first pitch diameter A may be pre-selected such that a plurality of turns 474 of coil 472 will contact outer surface 438 of second elongate shaft 426. By way of a second example, second pitch diameter B may be pre-selected such that a plurality of turns 474 of coil 472 will contact inner surface 454 of first elongate shaft 424.

Figure 7:
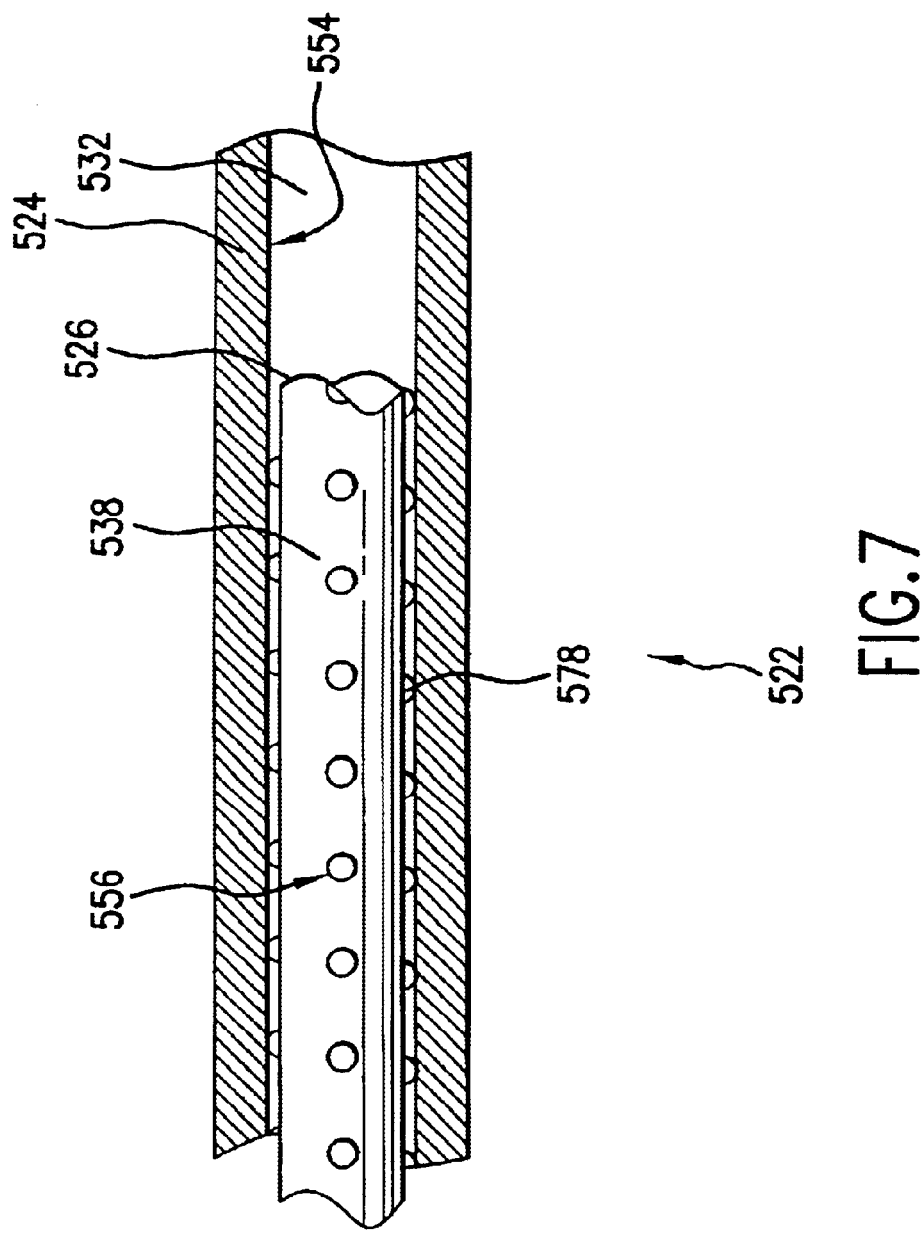
FIG. 7 is a partial cross section view of an additional embodiment of a shaft assembly in accordance with the present invention.

FIG. 7 is a partial cross section view of an additional embodiment of a shaft assembly 522 in accordance with the present invention. Shaft assembly 522 includes a first elongate shaft 524 having a lumen 532 defined by an inner surface 554 thereof A second elongate shaft 526 is disposed within lumen 532 of first elongate shaft 524. Second elongate shaft 526 includes an outer surface 538 and a plurality of interstitial members 556. In the embodiment of FIG. 7, each interstitial member 556 comprises a projection 578 extending beyond outer surface 538 of second elongate shaft 526.

Figure 8:
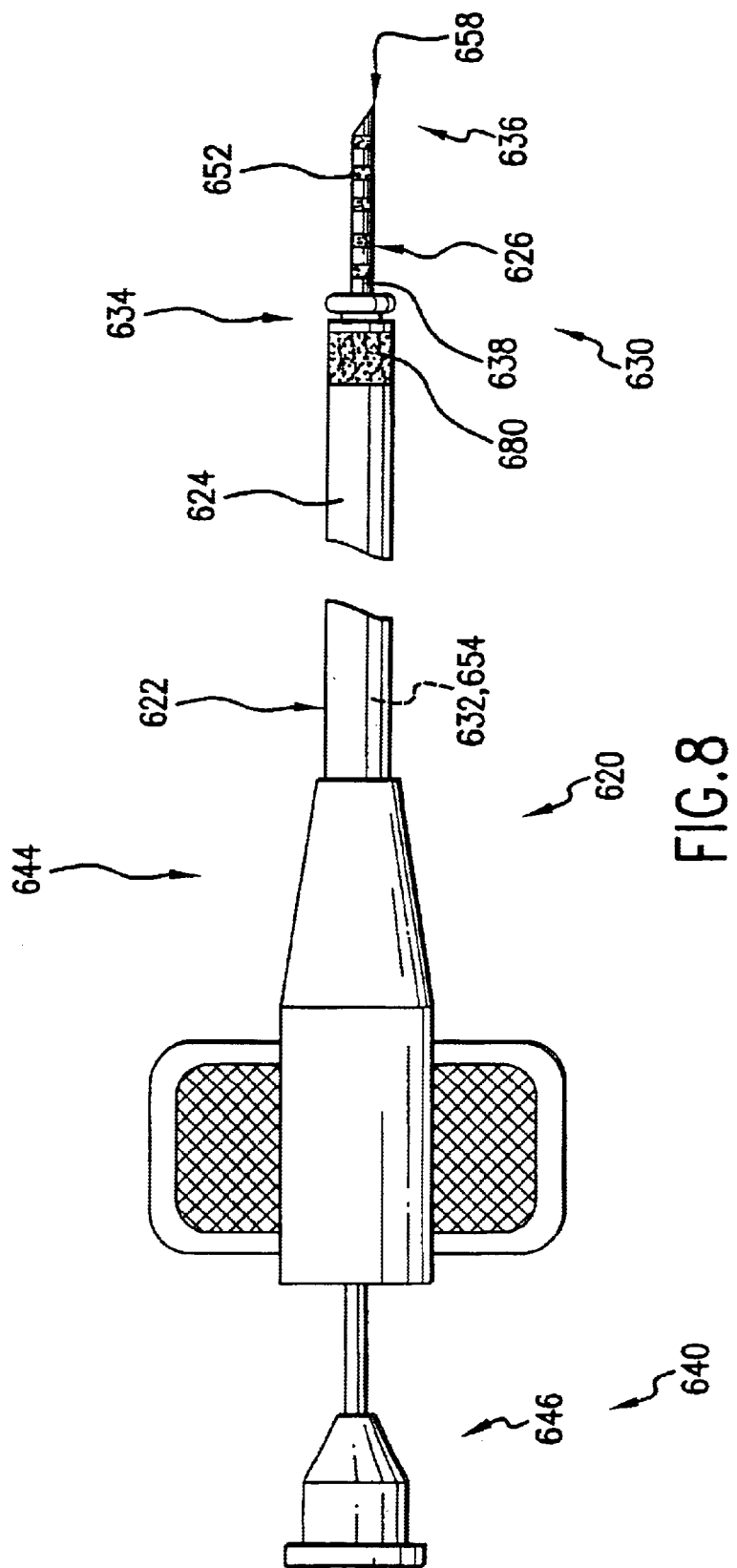
FIG. 8 is a plan view of an additional embodiment of a catheter in accordance with the present invention.

FIG. 8 is a plan view of an additional embodiment of a catheter 620 in accordance with the present invention. Catheter 620 has a distal end 630, a proximal end 640, and a shaft assembly 622. Shaft assembly 622 comprises a first elongate shaft 624 having a distal end 634, a proximal end 644, and an inner surface 654 defining a lumen 632. Shaft assembly 622 also includes a second elongate shaft 626 slidingly disposed within lumen 632 of first elongate shaft 624.

Second elongate shaft 626 has an outer surface 638, a distal end 636, and a proximal end 646. In many applications it is desirable to advance distal end 636 of second elongate shaft 626 by a known distance relative to distal end 634 of first elongate shaft 624. In the embodiment of FIG. 8, a plurality of indicia 652 are disposed on outer surface 638 of second elongate shaft 626 proximate a point 658 of second elongate shaft 626. In a preferred embodiment, indicia 652 are comprised of a radiopaque material. Examples of materials which may be suitable in some applications include gold, platinum, tungsten, iron, silver, and thermoplastic material loaded with a radiopaque filler. Examples of radiopaque filler which may be suitable in some applications include barium sulfate, bismuth subcarbonate, bismuth trioxide, bismuth oxychloride, tungsten, and depleted uranium.

A radiopaque reference 680 is disposed proximate distal end 634 of first elongate shaft 624. During surgery a radiopaque reference 680 and indicia 652 may be viewed on a fluoroscopy screen. The image viewed on the fluoroscopy screen may be utilized to determine the depth which point 658 has penetrated into the target tissue.

Figure 9:
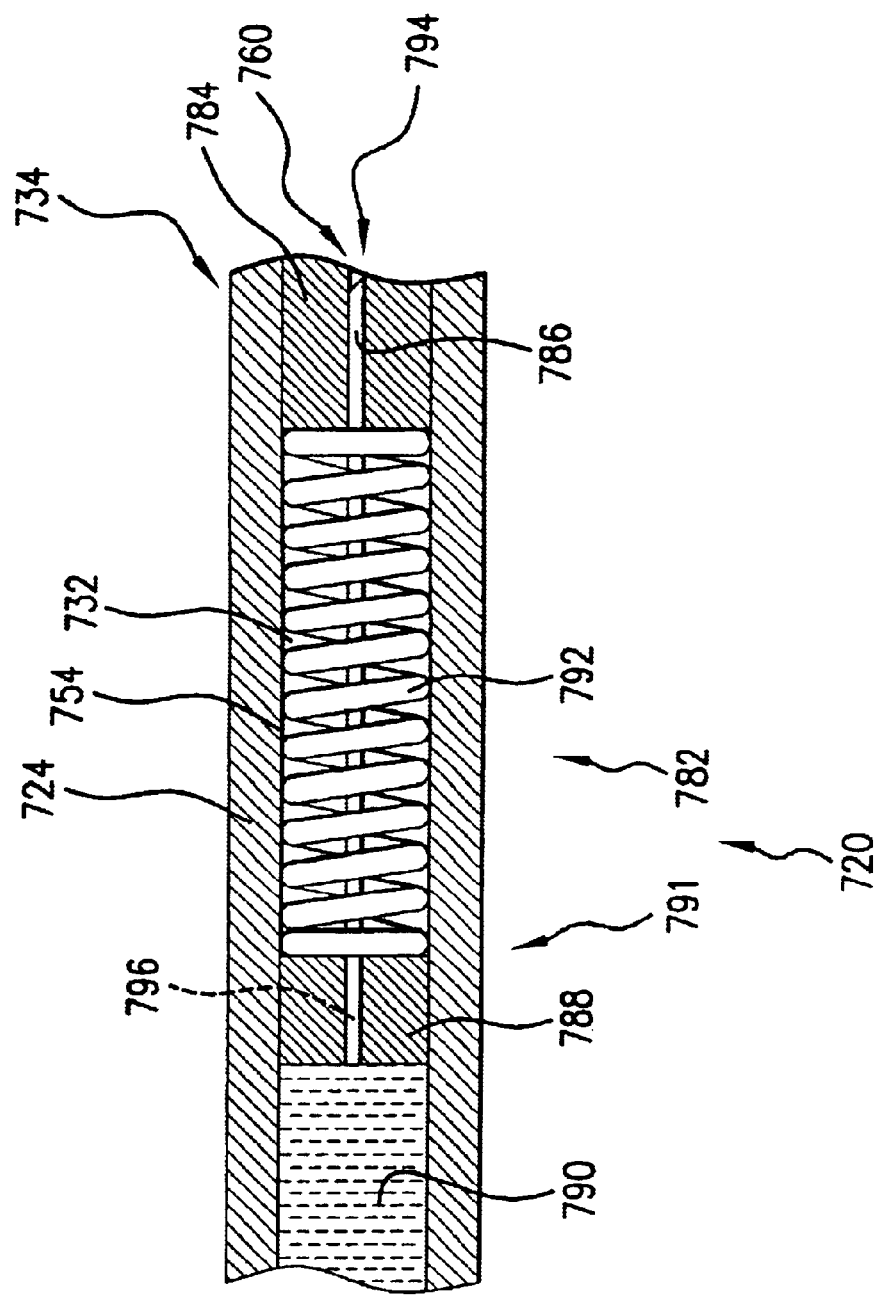
FIG. 9 is a cross sectional view of a distal portion of a catheter in accordance with the present invention.

FIG. 9 is a cross sectional view of a distal portion 782 of a catheter 720 in accordance with the present invention. Catheter 720 comprises a first elongate shaft 724 having an inner surface 754 defining a lumen 732. A ferrule 784 is disposed within lumen 732 proximate a distal end 734 of first elongate shaft 724. In a preferred embodiment, ferrule 784 is fixed to first elongate shaft 724. A needle 786 is slidingly disposed within a ferrule lumen 794 defined by ferrule 784. A piston member 788 is disposed about a proximal portion 71 of needle 786. Piston member 788 forms a sliding seal with inner surface 754 of first elongate shaft 724. A spring 792 is disposed within lumen 732 of first elongate shaft 724. In the embodiment of FIG. 9, the distal end of spring 792 is seated against ferrule 784 and the proximal end of spring 792 is seated against piston member 788.

In FIG. 9, a fluid 790 is disposed within lumen 732 of first elongate shaft 724 and a needle lumen 796 defined by needle 786. Catheter 720 of FIG. 9 may be utilized to inject fluid 790 into a target tissue. A fluid source may be utilized to urge additional fluid 790 into lumen 732 of first elongate shaft 724 and a needle lumen 796 defined by needle 786. In a preferred method, the additional fluid 790 is urged into lumen 732 with a velocity which is sufficient to create a pressure differential across piston member 788. In this preferred method, the pressure differential across piston member 788 is sufficient to compress spring 792 and urge an injection port 760 of needle 786 into the target tissue. In this manner a dose of fluid 790 may be injected into the target tissue. When the flow of fluid 790 stops, spring 792 will urge piston member 788 back to the position shown in FIG. 9.

Those of skill in the art will appreciate that many embodiments of the fluid source are possible without deviating from the spirit and scope of the present invention. For example, the fluid source may include a variable volume chamber in fluid communication with lumen 732 of first elongate shaft 724. In this exemplary embodiment, the fluid source may further include a plunger slidingly disposed within the variable volume chamber. Urging the plunger distally preferably has the effect of urging fluid into lumen 732 of first elongate shaft 724. A number of energy sources may be utilized to urge the plunger distally. Energy sources which may be suitable in some applications include springs, compressed gas, a human being, and electricity.

Figure 10:
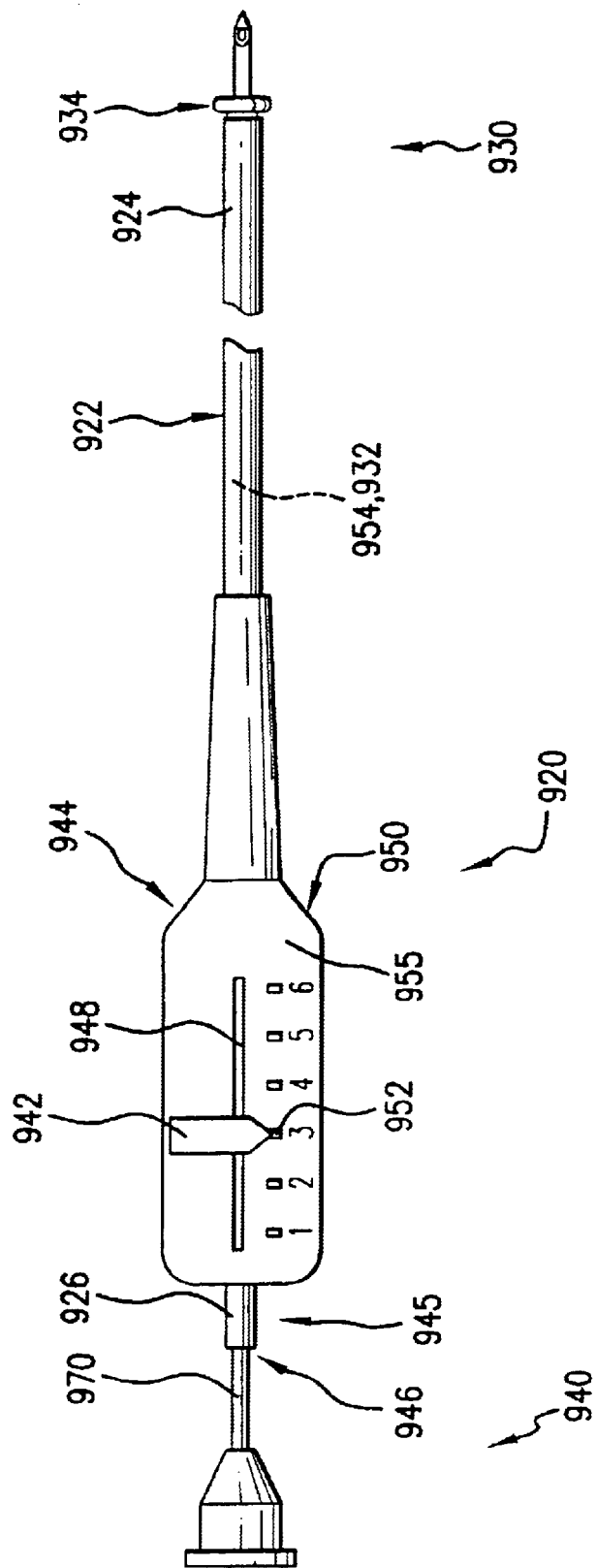
FIG. 10 is a plan view of a catheter including a shaft assembly in accordance with the present invention.

FIG. 10 is a plan view of a catheter 920 in accordance with the present invention. Catheter 920 includes a distal end 930, a proximal end 940, and a shaft assembly 922. Shaft assembly 922 comprises a first elongate shaft 924 having a distal end 934, a proximal end 944, and an inner surface 954 defining a lumen 932. Shaft assembly 922 also includes a second elongate shaft 926 slidingly disposed within lumen 932 of first elongate shaft 924, which may function as the interstitial member described above. A third elongate shaft 970 is slidingly disposed within a lumen defined by second elongate shaft 926. In the embodiment of FIG. 10, a proximal portion 945 of second elongate shaft 926 extends beyond proximal end 944 of first elongate shaft 924. Proximal portion 945 of second elongate shaft 926 terminates with a proximal end 946. Also in the embodiment of FIG. 10, a slider 942 is fixed to second elongate shaft 926 proximate proximal end 946 thereof. A portion of slider 942 is disposed within a cavity 948 (also referred to as a chamber) defined by a housing 950 (also referred to as a hub). In a presently preferred embodiment, housing 950 is fixed to first elongate shaft 924 proximate proximal end 944 thereof. Also in a preferred embodiment, a plurality of indicia 952 are disposed on a face 955 of housing 950 proximate slider 942.

Figure 11:
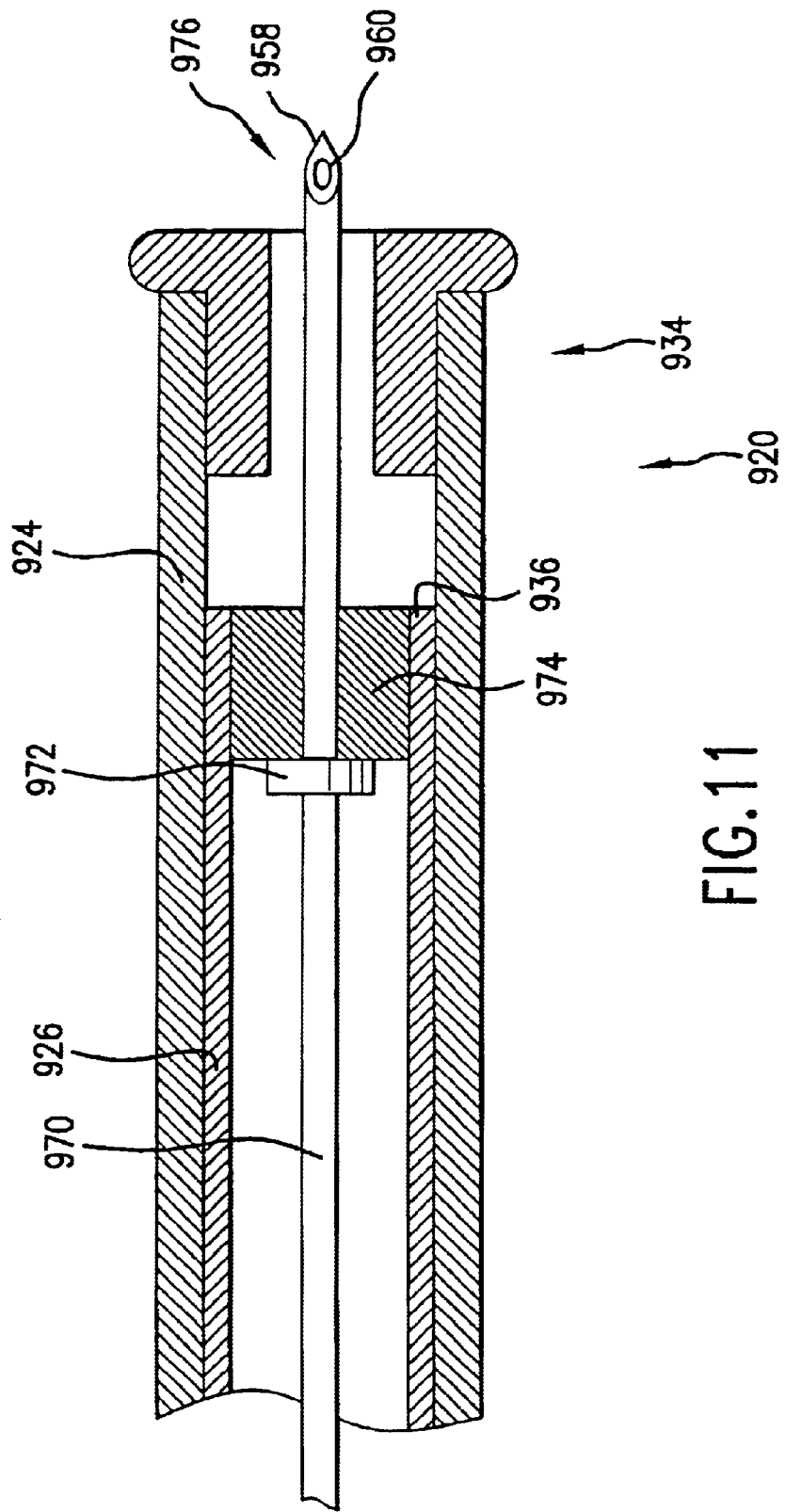
FIG. 11 is a partial cross section view of a distal portion of the catheter of FIG. 10.

FIG. 11 is a partial cross section view of a distal portion of catheter 920 of FIG. 10. As described previously, catheter 920 includes a first elongate shaft 924, a second elongate shaft 926, and a third elongate shaft 970. In a preferred embodiment, third elongate shaft 970 forms a point 958 proximate a distal end 976 thereof. Third elongate shaft 970 also defines an injection port 960 in fluid communication with an injection lumen. A flange 972 is disposed about third elongate shaft 970. Flange 972 cooperates with a mechanical stop 974 in order to limit the travel of third elongate shaft 970. In a preferred embodiment, mechanical stop 974 is fixed to second elongate shaft 926 proximate to distal end 936 thereof, forming an interstitial member between first elongate shaft 924 and third elongate shaft 970. The depth which elongate shaft 970 will penetrate into a target tissue (e.g., a heart wall) may be adjusted by moving distal end 936 of second elongate shaft 926 a known distance relative to distal end 934 of first elongate shaft 924. For example, a physician utilizing catheter 920 may urge slider 942 distally while visually observing the travel of slider 942 relative to indicia 952 of housing 950. In a preferred embodiment there is substantially a one-to-one relationship between the movement of slider 942 relative 952 to housing 950 and the movement of distal end 936 of second elongate shaft 926 relative to distal end 934 of elongate shaft 924. In the embodiment of FIG. 11, there is, preferably, interference fit between first elongate shaft 924 and second elongate shaft 926 to eliminate any slop, whether second elongate shaft 926 is tubular or comprises radial ribs, as illustrated in FIG. 11.

Figure 12:
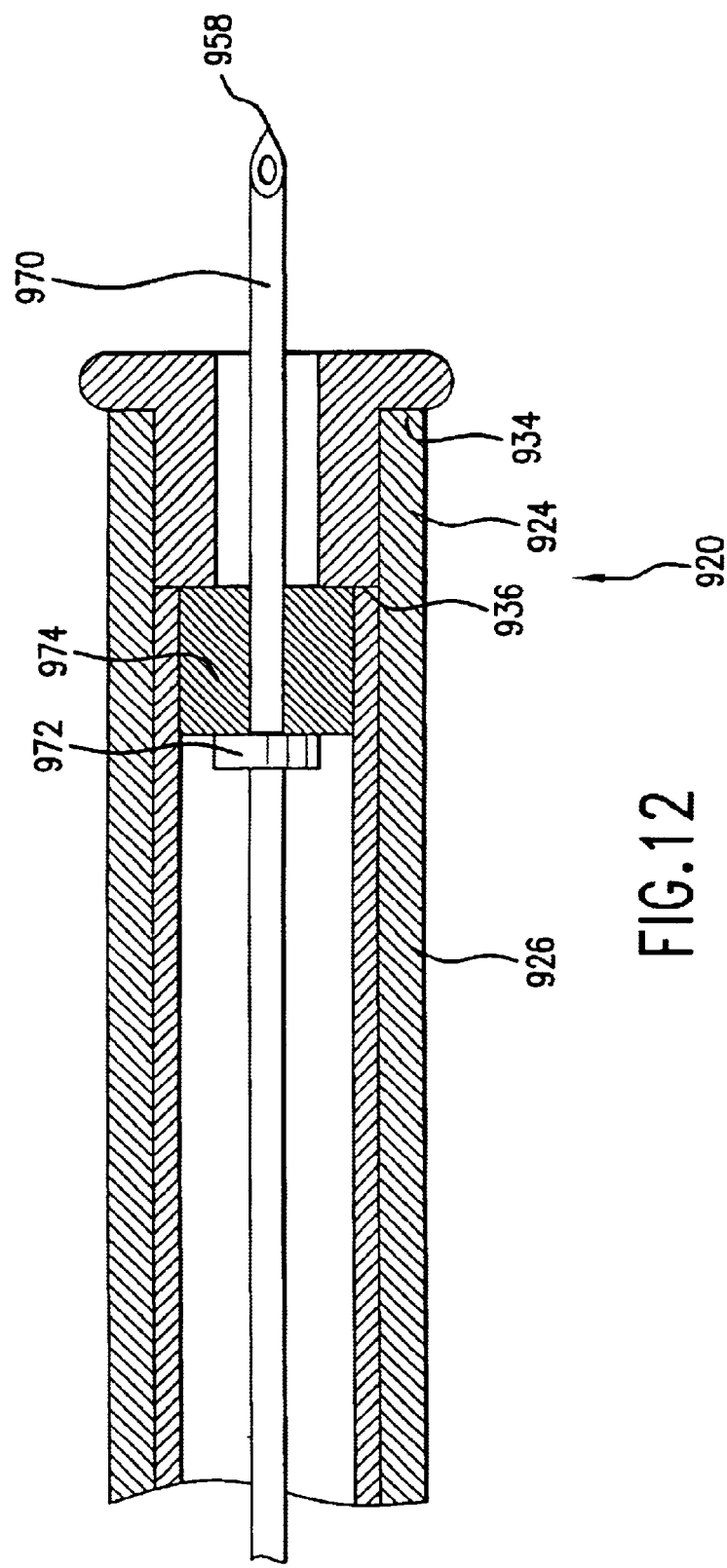
FIG. 12 is a partial cross section view of a distal portion of the catheter of FIG. 10.

FIG. 12 is a partial cross section view of a distal portion of catheter 920 of FIG. 10 and FIG. 11. In the embodiment of FIG. 12, distal end 936 of second elongate shaft 926 has been moved to a new position relative to distal end 934 of first elongate shaft 924. The position of second elongate shaft 926 illustrated in FIG. 12 may be referred to as a second position, and the position of second elongate shaft illustrated in FIG. 11 may be referred to as a first position. It is to be appreciated that second elongate shaft 926 may be urged proximally and distally to a plurality of positions. An injection may be performed by urging point 958 of third elongate shaft 970 distally into a target tissue. The advancement of third elongate shaft 970 into the target tissue may be stopped when flange 972 seats against mechanical stop 974.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter shaft assembly, comprising:
   a first elongate shaft having an inner surface defining a lumen;
   a second elongate shaft having an outer surface,
      the second elongate shaft slidingly disposed within the lumen of the first elongate shaft;
   an interstitial member disposed between the inner surface of the first elongate shaft and the outer surface of the second elongate shaft,
      the interstitial member having a proximal end, a distal end, an inner surface, and an outer surface,
         the inner surface of the interstitial member facing a portion of the outer surface of the second elongate shaft between the proximal and distal ends of the interstitial member, and
         the inner surface of the interstitial member shaped to engage only a portion of the portion of the outer surface of the second elongate shaft between the proximal and distal ends of the interstitial member;
   a housing disposed about the first elongate shaft proximate the proximal end thereof;
   a slider disposed about the second elongate shaft proximate a proximal portion thereof
   wherein the slider is disposed within a chamber defined by the housing;
   a plurality of indicia disposed upon a surface of the housing proximate the slider;
   the second elongate shaft forming a point at the distal end thereof;
   the second elongate shaft defining an injection port proximate the point thereof; and
   the second elongate shaft defining an injection lumen in fluid communication with the injection port.

2. The catheter of claim 1, wherein the interstitial member comprises a projection extending beyond the outer surface of the second elongate shaft.

3. The catheter of claim 1, wherein the interstitial member comprises a projection extending beyond the inner surface of the first elongate shaft.

4. The catheter of claim 1, wherein the interstitial member comprises a coil.

5. The catheter of claim 1, wherein the interstitial member comprises a coil disposed between the inner surface of the first elongate shaft and the outer surface of the second elongate shaft.

6. A catheter shaft assembly, comprising:
   a first elongate shaft having an inner surface defining a lumen;
   a second elongate shaft slidingly disposed within the lumen of the first elongate shaft;
   at least one interstitial member disposed between the inner surface of the first elongate shaft and the outer surface of the second elongate shaft,
      wherein the at least one interstitial member comprises a radial rib extending beyond the inner surface of the first elongate shaft;
   a housing disposed about the first elongate shaft proximate the proximal end thereof;
   a slider disposed about the second elongate shaft proximate a proximal portion thereof
      wherein the slider is disposed within a chamber defined by the housing;
   a plurality of indicia disposed upon a surface of the housing proximate the slider;
      the second elongate shaft forming a point at the distal end thereof;
      the second elongate shaft defining an injection port proximate the point thereof; and
      the second elongate shaft defining an injection lumen in fluid communication with the injection port.

* * * * *